United States Patent [19]

Wolters et al.

[11] Patent Number: 5,717,089
[45] Date of Patent: Feb. 10, 1998

[54] PROCESS FOR THE PREPARATION OF E-CAPROLACTAM

[75] Inventors: Henricus F. W. Wolters, Echt, Netherlands; Samuel L. Lane, Beaumont, Tex.; Wim Buijs, Schinnen, Netherlands; Frank E. Herkes, Wilmington, Del.; Nicolaas F. Haasen, Sittard, Netherlands

[73] Assignees: DSM N.V., Heerlen, Netherlands; E.I. Du Pont Nemours and Company, Wilmington, Del.

[21] Appl. No.: 616,748

[22] Filed: Mar. 15, 1996

Related U.S. Application Data

[63] Continuation-in-part of Ser. No. 396,240, Mar. 1, 1995, abandoned, and a continuation-in-part of Ser. No. 565,594, Nov. 30, 1995, abandoned.

[51] Int. Cl.[6] .................................................. C07D 201/08
[52] U.S. Cl. .................................................. 540/538
[58] Field of Search .................................................. 540/538

[56] References Cited

U.S. PATENT DOCUMENTS

| | | | |
|---|---|---|---|
| 3,485,821 | 12/1969 | Sheehan | 260/239.3 |
| 3,652,549 | 3/1972 | Fujita et al. | 540/538 |
| 4,730,040 | 3/1988 | Vagt et al. | 540/538 |
| 4,730,041 | 3/1988 | Hutmacher et al. | 540/538 |
| 4,731,445 | 3/1988 | Hutmacher et al. | 540/538 |
| 4,766,237 | 8/1988 | Hutmacher | 560/155 |
| 4,950,429 | 8/1990 | Vagt | 260/404 |
| 4,963,672 | 10/1990 | Merger et al. | 540/538 |
| 5,055,618 | 10/1991 | Kampmann | 564/473 |
| 5,068,398 | 11/1991 | Merger | 560/156 |
| 5,475,141 | 12/1995 | Kos | 564/473 |

FOREIGN PATENT DOCUMENTS

| | | | |
|---|---|---|---|
| 0 628 535 | 12/1994 | European Pat. Off. | C07C 209/26 |
| 47-10715 | 5/1972 | Japan | C07C 209/26 |
| 4-329148 | 11/1992 | Japan | C07C 209/26 |

*Primary Examiner*—Robert T. Bond
*Attorney, Agent, or Firm*—Cushman Darby & Cushman IP Group of Pillsbury; Madison & Sutro, LLP

[57] ABSTRACT

Process for the preparation of ε-caprolactam starting from an aldehyde compound comprising at least one member from among 5-formylvaleric acid, ester or amide in which the aldehyde compound is allowed to react in the presence of ammonia and hydrogen and a subsequent cyclization of the reaction products thus formed (ε-caprolactam-precursors) to ε-caprolactam is performed in the presence of water, involved the combination of steps (a) contacting the 5-formylvaleric acid, ester or amide with ammonia and water under non-hydrogenation conditions, (b) contacting the resulting mixture of step (a) with hydrogen in the presence of ammonia under hydrogenation conditions, wherein the water content is greater than 10 wt. %, (c) heating the resulting mixture of step (b) at a temperature between 200° and 350° C. in order to convert the reaction products of step (b) to ε-caprolactam.

15 Claims, 1 Drawing Sheet

PROCESS FOR THE PREPARATION OF ε-CAPROLACTAM

RELATED APPLICATIONS

This application is a continuation in part of applications Ser. Nos. 08/396,240 filed Mar. 1, 1995 and 08/565,594 filed Nov. 30, 1995, the complete disclosures of which are incorporated herein by reference. Both applications are now abandoned.

FIELD OF THE INVENTION

The present invention relates to the preparation of ε-caprolactam starting from a 5-formyl-valeric acid, ester or amide (called herein aldehyde compound). The aldehyde compound is reacted in the presence of ammonia, hydrogen, and water to yield ε-caprolactam and ε-caprolactam precursors. Cyclization of the precursors yields ε-caprolactam.

BACKGROUND OF THE INVENTION

An ε-caprolactam preparation process starting from methyl 5-formylvalerate is described in U.S. Pat. No. 4,730,040. In this process, methyl 5-formylvalerate is first hydrolyzed (step x) in the presence of water and an acidic agent to yield 5-formylvaleric acid. The acid is then further reacted (step y) in aqueous solvent with ammonia and hydrogen in the presence of a Raney nickel catalyst in one reaction step to yield 6-aminocaproic acid. After separation of ammonia, the aqueous mixture is heated to 300° C. (step z) to form ε-caprolactam by cyclization of the 6-aminocaproic acid.

Disadvantages to this process include relatively poor yields of ε-caprolactam which prevent it from being a commercially attractive process. According to the experimental results, the best yield of step (x) is only about 78%, the best yield of step (y) is only about 77% and the best yield of the final step (z) is only about 95%. Hence, the overall yield is at most 57%.

Another ε-caprolactam preparation process starting from a 5-formylvalerate ester is described in JP-B-68029148. A one step process is described in which a 5-formylvalerate is reacted with ammonia and hydrogen in the presence of water at 230° C. and 15 MPa in the presence of Raney nickel in the liquid phase. A disadvantage of this process, according to U.S. Pat. No. 4,730,041, is that the yields are erratic, e.g., fluctuate quite greatly, when the process is carried out industrially.

Therefore there has been need for a facile process for producing ε-caprolactam in a high yield starting from 5-formylvaleric acid, or the corresponding ester or amide of the acid.

SUMMARY AND OBJECTS OF THE INVENTION

An object of the present invention is a process for reproducibly preparing ε-caprolactam in high yield starting from 5-formylvaleric acid, or the corresponding ester or amide of the acid. This and other objects of the invention are achieved by performing the following steps:

(a) contacting the 5-formylvaleric acid, ester or amide with ammonia and water under non-hydrogenation conditions to obtain an aqueous reaction mixture, (b) contacting the aqueous reaction mixture from step (a) with hydrogen in the presence of ammonia under hydrogenation conditions, wherein the water content is greater than about 10 wt. % to obtain a mixture including ε-caprolactam precursors, (c) heating the mixture from step (b) to a temperature between 200° and 350° C. to effect cyclization of ε-caprolactam precursors to ε-caprolactam.

High yields to ε-caprolactam are obtained starting from the 5-formylvaleric acid, ester or amide when the process is performed in the above described fashion.

A further advantage of this process is that the solvent of the process is water. Water is a reaction product of the reactions taking place in the process according to the invention. By using additional water as a solvent, the number of different compounds in the process is limited. Furthermore, water is easily handled in large scale commercial plants. Less safety measures are needed when water is the solvent because it is, for example, non-toxic, non-explosive and non-carcinogenic. Another advantage is that the same solvent is used in the whole process making it possible to use the reaction mixture obtained in one step without undue burden in the next step.

A further advantage is that high yields to ε-caprolactam are possible when applying a relatively high concentration (concentration levels higher than 10 wt. %) of starting or intermediate compounds in the various steps (a)–(c). This is advantageous because lower-volume process equipment is needed which reduces the costs of investment for a commercial process.

The aforementioned and other advantages of the present process are obtained despite its being contrary to available literature. The process described in U.S. Pat. No. 3,485,821 is known for the cyclization of 6-aminocaproic acid or 6-aminocaproic acid amide (intermediate products of the present invention which are formed in step (b)) in an aqueous ammonia or in pure water solvent. However, experimental results show that polyamide is formed as a by-product at 33 wt. % 6-aminocaproic acid in water at 300° C.

Another process described in Mares et al., Ind. Eng. Chem. Process Des. Dev. Vol. 17, No. 1, 1978, page 9–16, involves the cyclization of 6-aminocaproic acid, ester and amide in either a water solvent or an ethanol solvent. However, this latter article teaches that high levels of dimers and other oligomers, which are disadvantageous, may be formed at a temperature of about 300° C. and at higher concentrations of 1 mol/kg of 6-aminocaproic acid or 6-aminocaproic acid amide in water. According to this article, oligomer formation is disadvantageous from the vantage point of the desired ε-caprolactam yield.

DESCRIPTION OF THE FIGURES

An embodiment of a preparation process starting from methyl 5-formylvalerate according to the present invention is depicted in FIG. 1.

DETAILED DESCRIPTION OF THE PRESENT INVENTION

Figure 1:
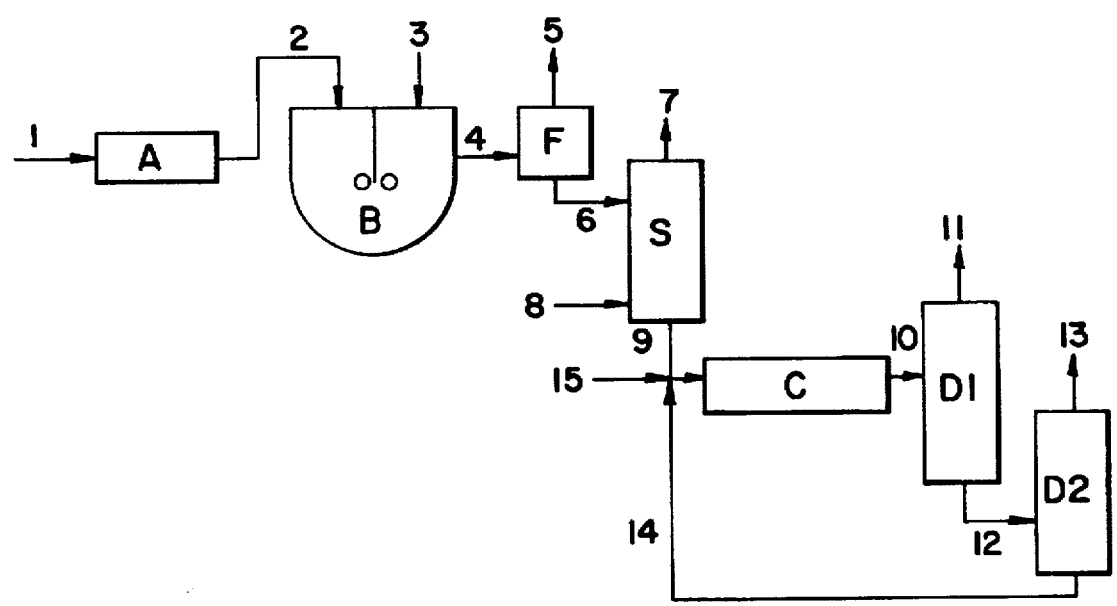

Starting compounds in the present process, 5-formylvalerate ester, 5-formylvaleric acid and 5-formylvaleric acid amide, will be referred to as the aldehyde compound. The term "aldehyde compound" encompasses all three starting compounds or mixtures of these compounds.

The mixture of compounds obtained in present step (b) will contain reaction products which are able to react to ε-caprolactam and possibly some amount of ε-caprolactam. The ε-caprolactam precursors are 6-aminocaproate ester, 6-aminocaproic acid and 6-aminocaproic acid amide. The amount of 6-aminocaproate ester will normally be very low.

When relatively high concentration of aldehyde compound is applied in step (a) and (b), a significant amount of oligomers (mostly dimers) of the foregoing compounds are also formed. It has been surprisingly found that these oligomers can be reacted to ε-caprolactam in step (c) with similar high yields compared to when starting from the three ε-caprolactam precursors listed above. Because of this, the oligomers formed in the present process of our invention are also considered to be ε-caprolactam precursors.

The 5-formylvalerate ester, acid or amide can be obtained by hydroformylation of the corresponding pentenoate ester, acid or amide as described, for example, for the ester in WO-A-9426688 and WO-A-9518089 and for the acid in WO-A-9518783, the complete disclosures of which are incorporated herein by reference. Preferably the 5-formylvalerate ester is the starting compound because this compound is more easily obtainable.

The aldehyde compound can be represented by the following general formula:

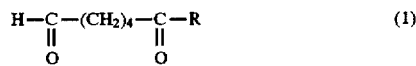

$$H-\underset{\underset{O}{\|}}{C}-(CH_2)_4-\underset{\underset{O}{\|}}{C}-R \quad (1)$$

where R is a —OH, —NH$_2$ or —O—R$^1$ group. R$^1$ is preferably an organic group with 1 to about 20 carbon atoms. The organic group can be an alkyl, cycloalkyl, aryl or aralkyl group. R$^1$ is more preferably an alkyl group. Exemplary R$^1$ groups include methyl, ethyl, propyl, isopropyl, n-butyl, tert-butyl, isobutyl, cyclohexyl, benzyl and phenyl, although methyl or ethyl are preferred.

Step (a) is carried out under non-hydrogenating conditions. The term 'non-hydrogenating conditions' means that the reaction conditions are such that, either no hydrogen is present or if hydrogen is present, then the aldehyde compound or a reaction product of it is not or virtually not reduced by the hydrogen. In general, non-hydrogenating conditions are realized by carrying out step (a) in the absence of a hydrogenation catalyst.

In one such embodiment of the present process, the hydrogen of step (b) can be already present in step (a). However, if the hydrogenation catalyst is already present in step (a), non-hydrogenating conditions are achieved by not adding hydrogen to the reaction mixture until after completing step (a). In a further embodiment, step (a) is conducted in the absence of hydrogen and a hydrogenation catalyst.

The temperature in step (a) can be up to about 120° C. A preferred temperature range is between about 0° C. and about 100° C., although a more preferred temperature is in the range of between about 20° C. to about 100° C.

We have also discovered that the best results with regard to yield to ε-caprolactam precursors are achieved when the conversion of the aldehyde compound in step (a) is greater than about 90%. By preference, the converesion is greater than about 99%. When conversions are too low, increased formation of, for example, the 6-hydroxycaproate ester (or acid or amide) and/or secondary amines is obsereved. Formation of these compounds can adversely influence the overall yield to ε-caprolactam.

Undesirable by-product formation can also occur when the contact or residence time in step (a) is insufficient. The optimal residence or contact time at which the conversion of the aldehyde starting compound is virtually completed (more than 90% or preferably more than 99% completed) will depend on the reaction conditions such as, for example, temperature, concentration of reactants and method of mixing. Longer contact or residence times beyond what are necessary to achieve the desired conversion can, if desired, be employed. The suitable residence time or contact time can be easily determined by those skilled in the art based on the disclosure herein. Based on the temperature and concentration ranges described herein practiced while operating under the usual mixing conditions, a suitable residence or contact time has been found to be longer than about several seconds, e.g. 5 seconds, up to several minutes. By preference, the residence or contact time is less than about 2 minutes, and more than about 5 seconds.

Step (a) is carried out in the presence of ammonia. Preferably a molar excess of ammonia is selected such that the molar ratio ammonia:aldehyde compound is between about 1:1 and about 500:1 calculated on the starting amount of the aldehyde compound. This ratio is preferably greater than about 5:1, although the ratio is more preferably greater than about 10:1. If this ratio is too low the ε-caprolactam yield is negatively influenced.

The reaction between the aldehyde compound and ammonia in step (a) produces water as a by-product. The amount of water in the starting mixture of step (a) and the water formed in step (a) is preferably sufficient such that the the mixture used in step (b) contains at least the about 10 wt. % water. More preferably step (a) is performed in the presence of at least about 10 wt. % water.

An alkanol is preferably present in step (a) when the aldehyde starting compound is a 5-formylvalerate ester. The alkanol can be the corresponding alcohol of the ester (R$^1$—OH). The concentration of alkanol in step (a) is preferably between about 2 and about 20 wt. %, and more preferably between 5 and 15 wt. %. The solubility of the 5-formylvalerate ester in the reaction medium increases when an alkanol is present in step (a).

Preferably the molar ratio ammonia:5-formylvalerate (5-formylvalerate plus ε-caprolactam and/or ε-caprolactam precursors) in step (a) is between about 3:1 and about 25:1. More preferably it is between 5:1 and 15:1.

The water content of the reaction mixture in step (a) is preferably between about 15 to about 60 wt. %, and more preferably, is between about 20 to about 50 wt. %.

The concentration of the aldehyde compound or the concentration of the sum of aldehyde compound and its reaction products (5-formylvalerate plus ε-caprolactam and/or ε-caprolactam precursors) in step (a) is generally between about 1 and about 50 wt. %, and preferably is between about 10 and about 35 wt. %.

In principle, the pressure in the first step is not critical. The pressure is generally equal or greater than the resulting equilibrium pressure of the reaction mixture and the temperature employed.

Step (a) can be carried in the presence of a catalyst such as an acid ion exchanger or an acidic metal oxide catalyst such as, for example alumina or TiO$_2$. The conversion of the aldehyde starting compound in the first step also proceeds favorably in the absence of a catalyst. A catalyst is generally not required in the first step because the overall yield to ε-caprolactam is not greatly influenced by the presence of a catalyst.

The process according to the invention can be performed batch wise or continuously. A large scale commercial process will preferably be performed continuously. For step (a), it is important that the reactants are sufficiently contacted at a certain temperature during a specified period of time optionally in the presence of a catalyst as described above. Any manner of contacting will usually suffice. For example, contacting units useful in practicing step (a) include a tube reactor with or without, for example, internal baffling or packing or a static mixer. The temperature in step (a) can be, if desired, controlled by using cooling devices such as cooled walls or a cooling spiral placed in or in combination with the contacting unit.

The above described ratios and concentrations and their preferred values for step (a) also apply for step (b) unless otherwise mentioned. Moreover the composition of the aqueous reaction mixture obtained in step (a) is, by preference, directly and without substantial separation of any of the compounds of the mixture used in step (b). This is advantageous because it results in a more simple process.

The reaction product obtained in step (a) is converted in step (b) to ε-caprolactam and ε-caprolactam precursors under hydrogenating conditions in the presence of ammonia.

The ε-caprolactam precursors, 6-aminocaproic acid amide, 6-aminocaproate ester or 6-aminocaproic acid, are represented by the following formula:

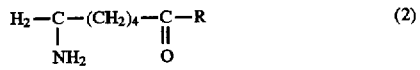
(2)

where R is the same as in formula (1). Oligomers are for the most part dimers of 6-aminocaproic acid or dimers of 6-aminocaproic acid amide. Trimers and higher oligomers can also be formed.

When the aldehyde compound is 5-formylvalerate ester, a mixture of ε-caprolactam, 6-aminocaproic acid, 6-aminocaproic amide and some (a small amount) or none of 6-aminocaproate ester and/or oligomers and the corresponding alcohol will be obtained in step (b). The hydrolysis or reaction of the ester-group essentially occurs in step (b). When the aldehyde compound is 5-formylvaleric acid, a mixture of ε-caprolactam, 6-aminocaproic acid and possibly some 6-aminocaproic acid amide and possibly some oligomers will be obtained in step (b). Starting from 5-formylvaleric acid amide the main product will be 6-aminocaproic acid amide and possibly some oligomers besides some ε-caprolactam.

The expression "hydrogenating conditions" means that the reaction conditions are such that the intermediate reaction product(s) obtained in step (a) can be reduced by hydrogen. In general, hydrogenation conditions are achieved when hydrogen and a hydrogenation catalyst are both present.

The total pressure used in step (b) is generally between about 0.5 and about 20 MPa. The pressure is preferably between about 0.5 to about 10 MPa and more preferably is between about 1.0 to about 5.0 MPa.

Step (b) is generally carried out at a temperature greater than about 40° C. The temperature is also generally lower than about 200° C. The temperature is more preferably between about 70° and about 180° C. and most preferably between about 80° and about 160° C. to achieve preferred yields of ε-caprolactam.

The residence or contact time in step (b) should be of such a duration so that virtually all the intermediate products formed in step (a) are reduced to ε-caprolactam and ε-caprolactam precursors. Longer residence or contact times can lead to increased formation of ε-caprolactam and possibly oligomers. The residence or contact time is preferably between approximately a half minute to a couple of hours, e.g. 2 hours. When the process is carried out batch wise or in a continuously operated slurry reactor, the contact or residence time respectively will generally be greater than the residence time selected when a continuously operated tube reactor is used.

The hydrogenation catalyst comprises one or more of the metals selected from among the metals of groups 8–10 of the Periodic System of the Elements (Handbook of Chemistry and Physics, 70th edition, CRC Press, 1989–1990). These metals include, for example, nickel, cobalt, ruthenium, platinum and palladium. Ru-, Ni- or Co-containing catalysts are preferred. In addition to Ru, Co and/or Ni, the catalysts can also contain other metals such as Cu, Fe and/or Cr. The content of additional metals can be, for example, up to 20% by weight based on the total metal content. The catalytically active metals can, if desired, be applied onto a carrier. Suitable carriers include aluminum oxide, silica, titanium oxide, zirconium oxide, magnesium oxide and carbon. Non-carried metals can also be used. A non-carried metal can be a finely dispersed metal such as ruthenium. Preferred Ni- and Co-containing catalysts are Raney nickel and Raney cobalt optionally in combination with small amounts of another metal, for example Cu, Fe and/or Cr. Most preferred are ruthenium-containing catalysts. High yields to ε-caprolactam over an extended period of time are possible when using this class of catalysts. Exemplary ruthenium catalysts include finely dispersed ruthenium (a "non-carried metal") or ruthenium on a carrier such as a carbon or alumina carrier.

Step (b) may be performed continuously in a fixed bed reactor in which a heterogeneous hydrogenation catalyst is present. An advantage of this reactor is that the reactants are easily separated from the hydrogenation catalyst. Another manner of operating step (b) is by way of one or more continuously operated well-mixed contactors in series in which the hydrogenation catalyst is present as a slurry (slurry reactor). This manner of operation has the advantage that the heat of the reaction of step (b) can be easily controlled by, for example, a cooled feed or by way of internally placed cooling devices. Examples of specific and suitable slurry reactors are one or multiple staged bubble columns or a gas lift-loop reactor or a continuously stirred tank reactor (CSTR). The slurry-hydrogenation catalyst can be separated from the reaction mixture after step (b) using means known to those skilled in the art, including hydrocyclones and/or by filtration, and for example by cake- or cross-flow filtration.

The catalyst concentration in step (b) can be selected across a wide range. In a fixed bed reactor the amount of active metal per volume will be high whereas in a slurry reactor this concentration will generally be lower. In a continuously operated slurry reactor the weight fraction of catalyst (including the carrier) is typically between about 0.1 and about 30 weight % relative to the total content of the reactor. The weight fraction will depend, for example, on the use of a carrier and the kind of carrier.

Ammonia, hydrogen, the hydrogenation catalyst and the alkanol (if present) are preferably separated from the reaction mixture obtained in step (b) prior to step (c). Hydrogen and part of the ammonia can be advantageously separated by reducing the pressure and performing a gas/liquid separation. This separation can be accomplished, for instance, by a flash operation performed at between ambient pressure and 0.5 MPa. The recovered and separated hydrogen and ammonia can be recycled to steps (a) and (b).

In a subsequent step the alkanol can be separated. It has been discovered that it is advantageous to perform the cyclization step (c) in the presence of less than about 1 wt. % and more preferably less than about 0.1 wt. % of alkanol. Thus, it is advantageous to separate out the alkanol if the resulting mixture of step (b) contains an alkanol. It has also been found that the presence of alkanol during the cyclization promotes the formation of the corresponding N-alkyl caprolactam, an unwanted by-product. The presence of small quantities of these N-alkylated products, for example, N-methyl ε-caprolactam, in the final ε-caprolactam renders the ε-caprolactam less suitable for use as starting material for manufacturing nylon-6 fibers. Moreover, these N-alkylated products are difficult to separate from the final ε-caprolactam. Therefore, the present process offers the further advantage of avoiding or minimizing formation of these unwanted by-products.

Separating out the alkanol can be accomplished by methods known to a person skilled in the art, including, for example, distillation or stripping methods exemplified by steam stripping.

The alcohol preferably is removed by stripping the aqueous mixture with steam. In a commercial large scale process, the stripping preferably involves the continuous counter current contacting of the aqueous starting mixture with upflowing steam in a vertically positioned column. At the top of the column, a water/alcohol stream is obtained, and at the bottom of the column, an alcohol-poor aqueous product stream is obtained. Steam stripping is advantageous because the alcohols can be removed very effectively and because a convenient concentration of the ε-caprolactam precursors and ε-caprolactam in resulting aqueous mixture is obtained. In this process, ammonia is also quantitatively removed. The water/alcohol/ammonia thus obtained can be advantageously recycled to step (a).

The steam stripping is preferably performed at a pressure between ambient pressure and about 1.0 MPa, and more preferably, under near atmospheric conditions. Near atmospheric conditions are preferred because less expensive process equipment is required.

In step (c), cyclization of ε-caprolactam precursors to ε-caprolactam occurs. The concentration of ammonia in step (c) is preferably below about 5 wt. %, and is more preferably, below about 3 wt. %. High concentrations of ammonia have a negative effect on the yield to ε-caprolactam (per pass).

The concentration of ε-caprolactam precursors in step (c) is preferably between about 5 to about 50 wt. % and is more preferably between about 10 to about 35 wt. % and is most preferably above about 15 wt. %.

The temperature in step (c) is between about 200° and about 350° C. By preference the temperature is between about 270° C. and about 330° C. More preferably, the temperature is higher than 285° C., because higher selectivity to ε-caprolactam and thus a higher overall yield to ε-caprolactam are obtained. Temperatures exceeding about 330° C. are possible, but are less preferred due to the increased formation of unwanted by-products.

The pressure in step (c) is preferably between about 5.0 and about 20 MPa. Normally this pressure will be greater than or equal to the resulting pressure of the reaction mixture and the temperature employed.

Step (c) can be performed continuously in process equipment resulting in high and low rates of back-mixing such as, for example, in a (optionally a series of) continuously stirred tank reactor(s) (CSTR) or a tube reactor.

The ε-caprolactam can be separated from the reaction mixture obtained in step (c) by, for example, crystallization, extraction or by distillation. Examples of possible extraction agents include methylene chloride, cyclohexane, toluene, benzene, chloroform and trichloro-ethane.

After separating the ε-caprolactam from the mixture obtained in step (c), the resulting mixture containing unconverted ε-caprolactam precursors comprising also some oligomers is preferably recirculated to step (c). Preferably not all of the ε-caprolactam is separated from the mixture obtained in step (c) if the ε-caprolactam is separated by distillation. It has been found that the oligomers are more easily handled when the distillation residue is mixed with some ε-caprolactam, preferably between about 5 and about 50 wt. % ε-caprolactam calculated based on the total amount of ε-caprolactam and oligomers. By performing step (c) in this way, it has been found that almost no build-up of oligomers in the circulating mixture takes place and that an overall yield to ε-caprolactam from the cyclization step (c) which practically reaches 100% is possible.

FIG. 1 is a schematic representation of the process equipment used in the examples herein below. In FIG. 1, a mixture of methyl 5-formylvalerate/water/ammonia/methanol (1) is led to tube reactor (A) wherein step (a) is performed. The resulting aqueous reaction mixture (2) is fed to continuously stirred tank reactor (B) wherein step (b) is performed in the presence of a catalyst slurry. Hydrogen (3) is continuously or intermittently fed during step (b) wherein the desired hydrogen partial pressure is maintained at a constant value. From the aqueous reaction mixture obtained in step (b), the slurry catalyst is separated by filtration (not shown). Hydrogen and part of the ammonia are separated from the mixture (4) by flashing in flasher (F). Methanol and the residual ammonia are separated from (6) in a steam stripper (S) in which steam is supplied via (8). The resulting mixture (9) is fed to tube reactor (C) wherein step (c) is performed. Mixture (9) is fed together with recycle (14) and fresh water (15). From (10), first water is separated in distillation unit (D1). From the mixture (12), ε-caprolactam (13) is separated in a second distillation unit (D2). The residue mixture (14) contains ε-caprolactam and ε-caprolactam precursors comprising also some oligomers. This mixture (14) is recirculated to step (c). In the recirculating streams, purges will be present (not shown) to overcome possible build up of contaminants and by-products.

The present invention is further elucidated with use of the following non-limiting examples.

EXAMPLES

The composition of the resulting mixtures of the experiments are sometimes expressed in mol percentages. The molar percentage of a component is represented by the molar fraction (* 100%) of the molar amount of converted methyl 5-formylvalerate (M5FV) which contributes to that specific component. For example, if the starting amount of M5FV is 100 mol and the resulting mixture contains 50 mol ε-caprolactam and 25 mol dimers, then the molar contribution to ε-caprolactam will be 50 mol % and the molar contribution to the dimers will be 50 mol % (totaling 100 mol %). When no oligomers (dimers etc.) are present in the mixture, the above molar percentages are the same as the molar yield as expressed below:

$$\text{yield of component } x = \frac{\text{mol component } x \text{ formed}}{\text{mol M5FV converted}} \times 100\%$$

EXAMPLE I

At a pressure of 5.0 MPa, 45 g/hr (312 mmol/hr) of methyl 5-formylvalerate, 495 g/hr (27.5 mol/hr) of water and 360 g/hr (21 mol/hr) of ammonia was pumped through a tube which was cooled by a water bath so that a constant temperature of 35° C. was maintained in the tube. Almost no back mixing occurred and the (liquid) residence time was 15 seconds. The reaction mixture leaving the tube did not contain any significant amount of methyl 5-formylvalerate. The resulting mixture leaving the tube (first step) was fed to a continuously stirred tank reactor, a Hastelloy C autoclave of 1 liter liquid volume. The reactor was stirred at 1250 rpm. The pressure was kept constant at 5 MPa. The residence time was 60 minutes and the temperature was kept at 100° C. To the reactor a net amount of 10 g/hr of hydrogen was fed. The reactor was filled with 50 g of an unpromoted Raney Nickel catalyst (93 wt. % nickel and 7 wt. % aluminum, average particle size: 59 µm from Activated Metals Company (A5000)). The rate of the effluent was such that the level of the liquid in the reactor was kept at a constant height.

The effluent was analyzed by High Pressure Liquid Chromatography (HPLC) after 3 and 6 hours of operation. The results are summarized in Table 1. The yields after 3 and 6 hours of operation were comparable and within their respective error range. The conversion of methyl 5-formylvalerate was 100%.

TABLE 1

|  | 3 hours | 6 hours |
|---|---|---|
| 6-aminocaproic acid amide | 58.7[1] | 59.8 |
| 6-aminocaproic acid | 23.9 | 25.3 |
| methyl-6-aminocaproate | 0.4 | 0.0 |
| ε-caprolactam | 17.0 | 14.9 |

[1] Results in weight percentage.

As is clear from Table 1 high yields, up to a total of 100%, are obtained of ε-caprolactam and ε-caprolactam precursors when using water as solvent.

EXAMPLE II

Example I was repeated using 39.9 grams/hr of methyl 5-formylvalerate, 184 g/hr ammonia and 644 g/hr of water. The residence time in step (a) was 15 seconds and in step (b) 60 minutes. The catalyst concentration was 60 g/liter, and the liquid level was kept constant maintaining a liquid volume in the reactor of step (b) of 1 l.

After step (b) and gas/liquid separation at reaction conditions, the liquid reaction mixture thus obtained contained: no starting methyl 5-formylvalerate (100% conversion), 7.2 g/h methanol, 170 g/hr ammonia, 647 g/hr water, 12.6 g/hr 6-aminocaproic acid, 12 g/hr 6-aminocaproic acid amide, 4.3 g/hr ε-caprolactam.

The selectivity to ε-caprolactam and ε-caprolactam precursors of step (a) and step (b) was 81.9%.

EXAMPLE III

Example II was repeated using 38.7 g/hr methyl 5-formylvalerate, 299 g/hr ammonia and 407 g/hr water.

After the gas/liquid separation at reaction conditions, the liquid stream had the following composition: 8.5 g/hr methanol, 275 g/hr ammonia, 410 g/hr water, 8.7 g/hr 6-aminocaproic acid, 20.7 g/hr 6-aminocaproic acid amide and 4.8 g/hr ε-caprolactam.

The conversion of methyl 5-formylvalerate ester was 100% and the selectivity of step (a) and (b) was 99.7%.

Examples II and III illustrate the influence of the ammonia-water molar ratio on the selectivity to ε-caprolactam and ε-caprolactam precursors.

EXAMPLE IV-V

Example II was repeated at 2 MPa, with a catalyst concentration of 50 g/l with different feed compositions. The results are in Table 2:

TABLE 2

| Example nr. | M5FV g/h | NH$_3$ g/h | H$_2$O g/h | Selectivity % |
|---|---|---|---|---|
| IV | 42.6 | 93.3 | 770 | 93.4 |
| V | 40.4 | 173.6 | 639 | 97.5 |

EXAMPLE VI-IX

Example II was repeated at different hydrogen pressures with a catalyst concentration of 50 g/l. The results are in Table 3.

TABLE 3

| Example nr. | Pressure MPa | M5FV g/h | NH$_3$ g/h | H$_2$O g/h | selectivity |
|---|---|---|---|---|---|
| VI | 1.6 | 42.3 | 92.5 | 766 | 94.4 |
| VII | 2.0 | 42.6 | 93.3 | 770 | 93.4 |
| VIII | 3.0 | 42.4 | 93.8 | 761 | 90.8 |
| IX | 4.0 | 42.4 | 91.7 | 754 | 85.9 |

Examples I-IX illustrate that high selectivities and yields to ε-caprolactam and ε-caprolactam precursors can be achieved by varying, for example, the hydrogen pressure or the water-ammonia ratio.

EXAMPLE X

Example I was repeated for 50 hours at a pressure of 3 MPa in which 81.7 g/hr of M5FV, 203 g/hr ammonia and 526 g/hr water was pumped through the tube at a temperature of 35° C. Almost no back-mixing occurred in the tube and the liquid residence time in the tube was 15 seconds. The reaction mixture leaving the tube contained no M5FV.

The mixture leaving the tube was fed to the continuously stirred tank reactor (CSTR) in which a liquid hold-up of 1 liter of liquid was maintained. The catalyst in the CSTR was a 5 wt. % ruthenium on Al$_2$O$_3$ catalyst (Engelhard: ESCAT 44) and the catalyst concentration was maintained at 103 g/l. The CSTR was stirred at 1260 rpm. The pressure in the CSTR was kept constant at 3 MPa and the temperature at 120° C. The residence time was 60 minutes. To the reactor, a net amount of 5.0 g/hr of hydrogen was fed.

The effluent of the CSTR was analyzed by HPLC every 4 hours. The composition of the effluent did not vary significantly during the 50 hours of operation. The average composition of the effluent in the last 28 hours was 28 mol % 6-aminocaproic acid (6ACA), 47.2 mol % 6-aminocaproic acid amide (6ACAM), 24.2 mol % ε-caprolactam (CAP), 0.6 mol % methyl 6-aminocaproate (M6AC). No detectable amount of N-methyl caprolactam was present in this mixture. Thus, a 100 mol % yield to ε-caprolactam and ε-caprolactam precursors is obtained in step 1 and 2.

EXAMPLE XI

Example X was repeated for 22 hours in which the water feed was replaced by a mixture of water and methanol (15 wt. % methanol). The feed rate of this mixture was 511 g/hr. Almost no back-mixing occurred in the tube and the liquid residence time in the tube was 15 seconds. The reaction mixture leaving the tube contained practically no methyl-5-formylvalerate.

The catalyst concentration in the CSTR was 96.0 g/l.

The composition of the effluent did not vary significantly during the 22 hours of operation. The average composition of all the products formed in the last 12 hours was 22.5 mol % 6ACA, 48.0 mol % 6ACAM, 27.4 mol % ε-caprolactam, 2.1 mol % methyl 6-aminocaproate. No detectable amount of N-methyl caprolactam was present in this mixture. Thus, a 100 mol % yield to ε-caprolactam and ε-caprolactam precursors is obtained in step 1 and 2 when methanol is present in the feed to step 1.

EXAMPLE XII

Example XI was repeated for 34 hours at a pressure of 3 MPa wherein 154 g/hr of methyl-5-formylvalerate, 205 g/hr ammonia and 439 g/hr of the 15 wt. %-methanol/water mixture was pumped through the tube at a temperature of 35° C. Almost no back-mixing occurred in the tube, and the liquid residence time was 15 seconds. The reaction mixture leaving the tube contained no methyl-5-formylvalerate.

The catalyst concentration in the CSTR was 209 g/l and the net hydrogen feed to the CSTR was 10 g/h. The temperature and pressure were the same as in Examples X and XI. The residence time was 60 minutes.

The composition of the effluent did not vary significantly during the 34 hours of operation. The composition of all the products present in the effluent of the CSTR after 34 hours was 19.6 mol % 6ACA, 36.9 mol % 6ACAM, 31.5 mol % ε-caprolactam, 2.4 mol % methyl 6-aminocaproate and 9.6 mol % oligomers. Most of the oligomers (about 90 wt. % of the oligomers) were dimers of either 6ACA or 6ACAM. No N-methyl caprolactam was detected in this mixture. The yield to ε-caprolactam and ε-caprolactam precursors is 90.4 mol %. If all of the oligomers contribute to the final ε-caprolactam yield (after the cyclization step (c)) the yield of step (a) and (b) is practically 100 mol %.

This example illustrates that a high selectivity to ε-caprolactam and ε-caprolactam precursors is possible at a relatively high initial substrate concentration of 19.3 wt. % M5FV.

EXAMPLE XIII

Example XI was repeated for 22 hours at a pressure of 3 MPa, in which 192 g/hr of M5FV, 237 g/hr ammonia and 357 g/hr of the 15 wt. %-methanol/water mixture was pumped through the tube at a temperature of 35° C. Almost no back-mixing occurred in the tube and the liquid residence time was 15 seconds. The reaction mixture leaving the tube contained no M5FV.

The catalyst concentration in the CSTR was 209 g/l and the net hydrogen feed to the CSTR was 10 g/h. The temperature and pressure were the same as in Examples X and XI. The residence time was 60 minutes.

The mixture leaving the CSTR was mixed with 114 g/hr of water after which the pressure was reduced to ambient pressure in a flash operation. The additional water was added before the flash operation and provided additional cooling. The composition of the effluent did not vary significantly during the 22 hours of operation. The composition of all the products present in the effluent of the CSTR at 22 hours was 14 mol % 6ACA, 40 mol % 6ACAM, 34 mol % ε-caprolactam, 0 mol % methyl 6-aminocaproate and 12 mol % oligomers. Most of the oligomers (about 88 wt. % of the oligomers) were dimers of either 6ACA or 6ACAM. No detectable amounts of N-methyl caprolactam ware present in this mixture. The yield to ε-caprolactam and ε-caprolactam precursors is 88%. If all of the oligomers contribute to the overall ε-caprolactam yield, then the yield of the combined step (a) and (b) is 100 mol %.

This example illustrates that a 100% yield to ε-caprolactam and ε-caprolactam precursors is possible at a relatively high initial substrate concentration of 24.4 wt. % M5FV.

EXAMPLE XIV

The effluent of Example XII was continuously flashed over 34 hours at 0.11 MPa. Also, 100 grams/hr $H_2O$ was continuously fed to this flasher to provide additional cooling. The resulting liquid stream, after flashing, had a transfer rate of 612 grams/hr and contained 4.8 wt. % $NH_3$, 6.5 wt. % methanol, 66.0 wt. % $H_2O$ and a total of 21.7 wt. % of ε-caprolactam and ε-caprolactam precursors (1.07 mol/hr). After 34 hours 20.8 kg (36.4 mol ε-caprolactam or ε-caprolactam precursors) of this mixture was collected.

The collected mixture was subsequently continuously fed to a cyclization reactor at a rate of 500 grams/hr and at a temperature of 300° C. The cyclization was carried out in a plugflow reactor (almost no back-mixing) at a constant temperature of 300° C. (maintained with the use of an oil bath), a pressure of 10 MPa and at a residence time of 30 minutes. The effluent leaving the cyclization reactor was cooled down and depressurized to ambient conditions. The average composition of all the products present in the liquid aqueous stream amounted to 65.9 mol % CAP, 5.1 mol % N-methyl caprolactam, 3.6 mol % 6ACA, 7.2 mol % 6ACAM and 18.2 mol % oligomers.

By vacuum distillation $H_2O$, $NH_3$ and methanol were semicontinuously removed from this liquid aqueous mixture. From the bottom stream of the first distillation, 2515 grams ε-caprolactam (22.26 mol) and 234 grams N-methyl caprolactam (1.84 mol) were recovered by a second vacuum distillation. In the second distillation, 1464 grams of residue (bottom product) was obtained, which according to the mass-balance contained 12.3 mol equivalent monomeric products. Analysis of the residue showed that CAP, 6ACA, 6ACAM and oligomers were present.

This residue together with fresh water was fed continuously to the same cyclization reactor as described above. The rate of the residue was 100 grams/hr and the rate of the fresh water was 400 grams/hr. Cyclization of the residue was carried out at 300° C., 10 MPa and at a residence time of approximately 30 minutes. After cooling and depressurizing of the effluent of the cyclization reactor, the average composition of all the products present in the liquid aqueous stream amounted to 71.7 mol % ε-caprolactam, 10.9 mol % of 6ACA and 6ACAM and 17.4 mol % oligomers. No detectable amounts of N-methyl caprolactam were present in the product mixture.

With two vacuum distillations as described above, 924 grams of ε-caprolactam (8.18 mol) was recovered from the liquid aqueous stream. Also 489 grams of residue was obtained in the second distillation. According to the mass-balance should contain 4.11 mol caprolactam and/or caprolactam precursors.

The residue and fresh water was fed continuously to the same cyclization reactor as described above. The rate of the residue was 100 grams/hr and the rate of the fresh water was 400 grams/hr. Cyclization and distillation of the products was carried out as formerly described. The composition of all the products present in the aqueous effluent of the cyclization was again 71.7 mol % ε-caprolactam, 10.9 mol % 6ACA and 6ACAM and 17.4% oligomers. Again, no N-methyl caprolactam was detected. After distillation 309 grams of ε-caprolactam (2.73 mol) was recovered. The distillation residue (165 gr) should contain according to the mass-balance 1.38 mol ε-caprolactam and/or ε-caprolactam precursors.

Thus after 2 times recycle of the distillation residue, an overall caprolactam yield of 91.2 mol % had been achieved based on the initial amount of M5FV. In the first cyclization pass, where still some methanol was present, 5.1 mol % of the unwanted by-product N-methyl caprolactam was formed. The approximated caprolactam yield per pass was 61.2% in the first pass, 66.5% in the second pass (first recycle of distillation residue) and 66.4% in the third pass (second recycle of distillation residue). Thus, it was proven that after distillative caprolactam recovery the remaining distillation residue can be successfully recycled to the cyclization reactor resulting in a high overall caprolactam yield.

EXAMPLE XV

The resulting effluent of Example XIII was continuously fed for 22 hours to the top of a steamstripper column at a rate of approx 550 grams/hr. Steam was generated in a reboiler of the column. To the column, 350 grams/hr of fresh water was also fed. In the steamstripper column, the liquid product stream was thus contacted with an upflowing stream of steam. The bottom temperature in the column was kept at 100° C. The liquid bottom stream which left the steamstripper at a rate of 742 grams/hr did not contain any detectable amount of methanol and $NH_3$. The concentration of $\epsilon$-caprolactam and $\epsilon$-caprolactam precursors in the liquid bottom stream was 22.1 wt. % in water (1.33 mol/hr). After 22 hours, 16.3 kg of this mixture was collected containing a total of 29.26 mol of $\epsilon$-caprolactam and $\epsilon$-caprolactam precursors (3.3 wt. % 6ACA, 9.3 wt. % 6ACAM, 6.9 wt. % $\epsilon$-caprolactam and 2.6 wt. % oligomers).

This liquid mixture was fed continuously to the cyclization reactor as first described in Example XIV at a rate of approximately 500 grams/hr and a temperature of 300° C. The cyclization was carried out at 300° C., 10 MPa and at a residence time of approximately 30 minutes. After cooling and depressurizing, the average composition of all the products present in the liquid aqueous stream amounted to 70.5 mol % $\epsilon$-caprolactam, 10.8 mol % 6ACA(M) and 18.7 mol % oligomers. No N-methyl caprolactam was detected in this mixture.

In two consecutive semicontinuous distillations as described in Example XIV, first water was removed from the product stream, and second, 2164 grams of caprolactam (19.15 mol) was recovered from the product stream. The residue of the second distillation amounted to 1205 grams and according to the mass balance should contain a total of 10.13 mol of $\epsilon$-caprolactam and $\epsilon$-caprolactam precursors. The caprolactam yield in the first pass through the cyclization reactor was thus 65.4 mol %.

By removing the methanol prior to performing the cyclization step, the formation of N-methyl caprolactam can be avoided as illustrated by comparing this Example with Example XIV. Furthermore, a higher yield to $\epsilon$-caprolactam can be obtained for this illustrated situation wherein a cyclization is performed without including a recycle mixture in the feed of the cyclization (ones through) followed by a recycle experiment using the residue of the first cyclization (e.g. $\epsilon$-caprolactam) as feed of the second cyclization. Proven is that a high yield of $\epsilon$-caprolactam can be obtained from the feed of this experiment by further processing of the residue of a first cyclization in the manner as illustrated in this experiment.

EXAMPLE XVI

Example X was repeated with continuous feed composition of 24.4 wt. % M5FV, 30.2 wt. % $NH_3$, 6.8 wt. % methanol, and 38.6 wt. % $H_2O$ to a two step reductive amination section as described in Example X. The flow rate corresponded with 191.6 grams/hr M5FV (1.33 mol/hr).

The mixture leaving the CSTR was continuously flashed at 0.11 MPa. Also 114 grams/hr $H_2O$ was continuously fed before the flasher to provide additional cooling. The product composition of the resulting liquid stream (approx. 550 grams/hr) consisted of 31 grams/hr methanol, 25 grams/hr ammonia, 330 grams/hr $H_2O$ and 164 grams/hr products of which 14.2 mol % 6ACA, 39.9 mol % 6ACAM, 33.9 mol % CAP and 12.0 mol % oligomers.

This mixture was continuously fed to a steamstripper column as described in Example XV. Also 350 grams/hr $H_2O$ is fed to the steamstripper column (bottom temperature is maintained at approximately 100° C.). The remaining aqueous bottom stream having a rate of 742 grams/hr contained a total of 22.1 wt. % of $\epsilon$-caprolactam and $\epsilon$-caprolactam precursors (1.33 mol/hr).

This mixture was continuously fed to a cyclization reactor as first described in Example XIV. Also 85 grams/hr (approx 0.715 mol/hr) of a recycle distillation residue (see below) and 314 grams/hr $H_2O$ were fed to the cyclization reactor. Thus, overall 1141 grams/hr product mixture (21.8 wt. % products) was fed to the cyclization reactor (249 grams/hr $\epsilon$-caprolactam and $\epsilon$-caprolactam precursors and 892 grams/ hr $H_2O$).

The cyclization was carried out at 300° C., 10 MPa and at a residence time of approximately 30 minutes. After cooling and depressurizing, the effluent of the cyclization reactor was analyzed. The mixture consisted of 70.5 mol % $\epsilon$-caprolactam, 10.8 mol % 6ACA(M) and 18.7 mol % oligomers.

This cyclization mixture was continuously fed to 2 consecutive vacuum distillation columns. In the first column, the solvent ($H_2O$) was removed. From the second column, $\epsilon$-caprolactam was recovered at a rate of 150 grams/hr (1.33 mol/hr).

The distillation residue obtained as the bottom stream in the second distillation (containing approximately a total of 0.715 mol/hr $\epsilon$-caprolactam and $\epsilon$-caprolactam precursors) was continuously recycled to the cyclization reactor (see above) at a rate of 85 grams/hr.

Thus, virtually a 100% caprolactam yield could be obtained in a continuous reductive amination and cyclization process using a steamstripper to remove methanol before the cyclization and by recycling of the distillation residue after recovering part of the $\epsilon$-caprolactam.

The above results were obtained 3 hours after the continuous process stabilized.

While the invention has been described in detail and with reference to specific embodiments thereof, it will be apparent to those of ordinary skill in the art that various changes and modifications can be made therein without departing from the spirit and scope thereof.

What is claimed is:

1. A liquid phase process for the preparation of $\epsilon$-caprolactam starting from a 5-formylvalerate ester in the liquid phase, in which a reaction of said 5-formylvalerate ester in the presence of ammonia, hydrogen, and water to yield $\epsilon$-caprolactam-precursor reaction products followed by cyclization to form $\epsilon$-caprolactam is performed, which liquid phase process comprises the combination of steps of:

(a) contacting said 5-formylvalerate ester with ammonia and water under non-hydrogenation conditions, (b) contacting the resulting mixture of step (a) with hydrogen in the presence of ammonia and a hydrogenation catalyst comprising at least one metal selected from Group 8–10 of the Periodic System of Elements, wherein the water content of the reaction mixture from step (a) is higher than 10 wt. %, to obtain a mixture containing ε-caprolactam precursors, (c) heating the mixture from step (b) at a temperature between about 200° C. and about 350° C. to convert the ε-caprolactam precursors to ε-caprolactam.

2. A process according to claim 1, wherein the temperature in step (a) is between about 20° and about 100° C.

3. A process according to claim 1, wherein in step (a) the molar ratio of ammonia to 5-formylvalerate ester is between about 3:1 to about 25:1.

4. A process according to claim 1, wherein the content of the 5-formylvalerate ester and/or its products in step (a) and step (b) is between about 10 wt. % to about 35 wt. %.

5. A process according to claim 1, wherein the water content in the reaction mixture in step (a) and (b) is between about 15 wt. % to about 60 wt. %.

6. A process according to claim 1, wherein said hydrogenation catalyst comprises a ruthenium-containing hydrogenation catalyst.

7. A process according to claim 1, wherein the temperature in step (c) is between 285° and 330° C.

8. A process according to claim 1, wherein the 5-formylvalerate ester is represented by the following general formula

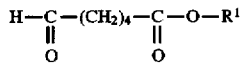

wherein $R^1$ is a 1 to 20 carbon atom alkyl group.

9. A process according to claim 8, wherein the starting mixture of step (a) contains an alkanol of the formula $R_1$—OH wherein $R^1$.Is a 1 to 20 carbon atom alkyl group.

10. A process according to claim 9, wherein the content of the alkanol in step (c) is less than 1 wt. %.

11. A process according to claim 1, wherein the process further comprises the steps of:

(d) separating ε-caprolactam from the mixture obtained in step (c) to obtain a remaining mixture comprising unconverted ε-caprolactam precursors; and (e) recycling said remaining mixture to a step (c).

12. A process according to claim 1, wherein the content of ε-caprolactam and ε-caprolactam precursors in step (c) is between about 10 wt. % and about 35 wt. %.

13. A process according to claim 12, wherein the content of ε-caprolactam and ε-caprolactam precursors is greater than about 15 wt. %.

14. A process according to claim 1, wherein the ammonia concentration in step (c) is below about 5 wt. %.

15. A liquid phase process for the preparation of ε-caprolactam starting from a 5-formylvalerate ester in the liquid phase wherein the solvent consists essentially of water, in which a reaction of said 5-formylvalerate ester in the presence of ammonia, hydrogen, and said solvent to yield ε-caprolactam-precursor reaction products followed by cyclization to form ε-caprolactam is performed, which liquid phase process comprises the combination of steps of:

(a) contacting said 5-formylvalerate ester with ammonia and said water under non-hydrogenation conditions, (b) contacting the resulting mixture of step (a) with hydrogen in the presence of ammonia and a hydrogenation catalyst comprising at least one metal selected from Group 8–10 of the Periodic System of Elements, wherein the water content of the reaction mixture from step (a) is greater than 10 wt. %, to obtain a mixture containing ε-caprolactam precursors, (c) heating the mixture from step (b) at a temperature between about 200° C. and about 350° C. to convert the ε-caprolactam precursors to ε-caprolactam.

* * * * *